United States Patent [19]

Scriabine

[11] 4,055,645
[45] Oct. 25, 1977

[54] NOVEL ANTI-HYPERTENSIVE COMPOSITIONS

[75] Inventor: Alexander Scriabine, Ambler, Pa.

[73] Assignee: Merck & Co., Inc., Rahway, N.J.

[21] Appl. No.: 657,825

[22] Filed: Feb. 13, 1976

[51] Int. Cl.$^2$ .................... A61K 31/50; A61K 31/15
[52] U.S. Cl. ..................................... 424/250; 424/327
[58] Field of Search .......................................... 424/250

[56] References Cited

U.S. PATENT DOCUMENTS

| | | | |
|---|---|---|---|
| 3,462,536 | 8/1969 | Chemerda et al. | 424/309 |
| 3,781,415 | 12/1973 | Karady et al. | 424/308 |
| 3,830,827 | 8/1974 | Karady et al. | 260/471 A |
| 3,839,585 | 10/1974 | Lotti et al. | 424/319 |

FOREIGN PATENT DOCUMENTS 737,907   2/1976   Canada

OTHER PUBLICATIONS

The Merck Index—Eighth Edition (1968), p. 538.

*Primary Examiner*—Sam Rosen
*Attorney, Agent, or Firm*—Daniel T. Szura; J. Jerome Behan

[57] ABSTRACT

Novel pharmaceutical compositions are disclosed which comprise a hypotensive agent and a phenyl hydrazino substituted propionic acid decarboxylase inhibitor. The compositions have enhanced anti-hypertensive activity.

5 Claims, No Drawings

NOVEL ANTI-HYPERTENSIVE COMPOSITIONS

BACKGROUND OF THE INVENTION

The present invention is directed to novel pharmaceutical compositions containing a hypotensive agent and a decarboxylase inhibitor.

The hypotensive agents of the present invention comprise agents, other than phenylalanine and reserpine type compounds, which are known to be effective in treating hypertension in humans. The decarboxylase inhibitor is encompassed in the class of hydrazino phenyl propionic acid compounds disclosed in U.S. Pat. No. 3,462,536; 3,830,827 and 3,781,415. Combinations of this hydrazino phenylpropionic acid type decarboxylase inhibitor with reserpine or phenylalanine type hypertensive agents are disclosed in Canadian Pat. No. 737,907 and U.S. Pat. No. 3,839,585.

It has now been discovered that the combination of the aforesaid non-phenylalanine, non-reserpine hypotensive agents with the hydrazino-phenyl propionic acid type decarboxylase inhibitors affords enhanced anti-hypertensive activity.

SUMMARY OF THE INVENTION

Novel pharmaceutical compositions comprising (a) a non-phenylalanine, non-reserpine hypotensive agent and (b) a D,L- or L-hydrazino-phenyl propionic acid decarboxylase inhibitor and a method of treating hypertensive animals.

DESCRIPTION OF THE PREFERRED EMBODIMENTS

An embodiment of this invention is a hypotensive pharmaceutical composition comprising
a. a non-phenylalanine, non-reserpine hypotensive agent and
b. the L-isomer or racemic mixture (D,L-) of a hydrazino phenylpropionic acid decarboxylase inhibitor.

Preferred hypotensive agents are selected from the group consisting of (1) spironolacetone, hydralazine, trimethaphan camsylate, clonidine, guanethidine, thiazide diuretics, cryptenamine, pharmaceutically acceptable salts thereof and (2) sodium nitroprusside. A more preferred group of hypotensive agents includes hydralazine, clonidine, guanethidine, the thiazide diuretics and pharmaceutically acceptable salts thereof. A most preferred group of hypotensive agents is clonidine, hydralazine, guanethidine and their pharmaceutically acceptable salts.

The thiazide diuretics include the benzothiadiazine class of compounds having the basic ring structure

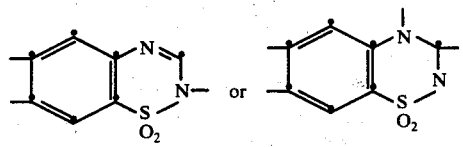

Representative compounds are disclosed in U.S. Pat. No. 2,809,184; 2,937,169; 3,025,292; 3,164,588 and 3,043,840, and are incorporated herein by references.

The preferred thiazide compounds are chlorothiazide, hydrochlorothiazide, trichlormethiazide, bendroflumethiazide, polythiazide, flumethiazide, and their pharmaceutically acceptable salts. Hydrochlorothiazide is a most preferred thiazide hypotensive agent.

Preferred decarboxylase inhibitors include the D,L-racemic mixture and the individual L-isomer of compounds having the formula:

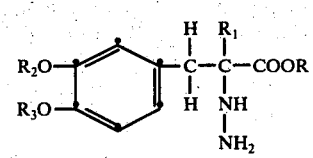

wherein R, $R_1$, $R_2$ and $R_3$ are independently selected from hydrogen and $C_1$–$C_4$ alkyl such as methyl, t-butyl, isopropyl and the like. A more preferred decarboxylase inhibitor is the L-isomer and most preferred is the L-isomer of

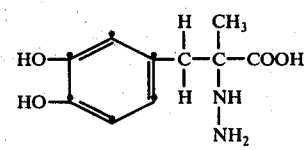

and its pharmaceutically acceptable salts. The monohydrate of IV is known as carbidopa.

Pharmaceutically acceptable salts include the salts of the various compounds with suitable organic or inorganic acids. Suitable organic acids are $C_2$–$C_{24}$ carboxylic acids such as acetic acid, maleic acid, pamoic acid, succinic acid, citric acid, propionic acid, isethionic acid, oxalic acid, pivalic acid and the like. Suitable inorganic acids include the hydrohalides, e.g., HCl, HI, HBr, sulfuric acid, phosphoric acid and the like. The salts may also be alkali metal salts such as the sodium or potassium salt or the ammonium salt.

The compositions of the present invention may contain varying amounts of the hypotensive agent and decarboxylase inhibitor. In general, the weight ratio of hypotensive agent (a) to decarboxylase inhibitor (b) will be from about 4:1 to about 1:9000. A preferred weight ratio of (a):(b) is about 1:1 to about 1:1000 and a most preferred weight ratio is about 1:5 to about 1:500.

In treating hypertension, a sufficient amount of the present composition is administered to the hypertensive animal to produce the desired hypotensive effect, i.e., reduction in blood pressure. Effective dosages may vary and can range from about 0.2 mg/kg to about 1000 mg/kg per day. The composition may be given as a single daily dose or divided into several smaller doses during the course of the day.

The composition may be administered parenterally or orally. The dosage form used will depend on the mode of administration. The oral form may be a tablet, a liquid solution, dispersion, or emulsion, a capsule, or an encapsulated composition—while the parenteral dosage form will generally be a liquid solution, suspension or emulsion. The dosage forms generally will include conventional carriers, diluents, either solid or liquid, dyes etc. and will be prepared using applicable formulation procedures.

The compositions of the present invention are administered to hypertensive animals to effect reduction in blood pressure. The decarboxylase inhibitors are known to have no appreciable anti-hypertensive effect. When combined with the present hypotensive agents, however, the anti-hypertensive effect of the hypotensive agent is unexpectedly enhanced.

This enhancement of anti-hypertensive activity is demonstrated in vivo in spontaneously hypertensive (SH) rats. The procedure used is as follows:

The test animals used were conscious, male, SH rats weighing about 290 to about 340 grams. The arterial blood pressure was measured by a direct technique involving cannulation of the caudal artery. Initial blood pressure reading was recorded. The decarboxylase inhibitor was then administered intraperitoneally (i.p.) and about 5 minutes later the hypotensive agent was given, (i.p.). The blood pressure was then continuously recorded at ½ hour intervals for 24 hours.

The effect on blood pressure of the decarboxylase inhibitor and the hypotensive agent alone was also obtained by this method. The results of these tests for representative compositions of the present invention are in the following tables:

Table 1

Effects of guanethidine and hydrochlorothiazide, alone and in combination with carbidopa, on the mean arterial pressure of conscious SH rats.

| Group No. | Treatment | Dose mg/kg i.p. | No. of Rats | Mean Arterial Pressure, mm Hg, at hours after treatment ||||||||| 
|---|---|---|---|---|---|---|---|---|---|---|---|---|
| | | | | 0 | ½ | 1 | 2 | 4 | 8 | 12 | 18 | 24 |
| 1 | Saline | 2 mg/kg | 9 | 168 | 170 | 170 | 170 | 166 | 164 | 166 | 166 | 164 |
| 2 | Carbidopa[1] | 25 | 6 | 167 | 166 | 164 | 166 | 158 | 167 | 172 | 172 | 162 |
| 3 | Guanethidine[2] | 0.078 | 6 | 179 | 178 | 177 | 177 | 174 | 180 | 180 | 177 | 178 |
| 4 | Guanethidine | 0.312 | 5 | 174 | 167 | 168 | 171 | 171 | 174 | 170 | 170 | 166 |
| 5 | Guanethidine | 0.625 | 4 | 176 | 180 | 180 | 178 | 172 | 179 | 173 | 174 | 176 |
| 6 | Guanethidine | 1.25 | 4 | 171 | 143 | 163 | 150 | 150 | 154 | 147 | 155 | 162 |
| 7 | Guanethidine | 5 | 4 | 174 | 131 | 133 | 132 | 140 | 157 | 155 | 163 | 162 |
| 8 | Carbidopa & Guanethidine | 25 0.312 | 4 | 173 | 161 | 162 | 173 | 166 | 172 | 171 | 172 | 170 |
| 9 | Carbidopa & Guanethidine | 25 0.625 | 6 | 173 | 157 | 140 | 137 | 137 | 144 | 152 | 147 | 149 |
| 10 | Carbidopa & Guanethidine | 25 1.25 | 4 | 166 | 126 | 133 | 129 | 126 | 141 | 147 | 158 | 157 |
| 11 | Hydrochlorothiazide[3] | 5 | 4 | 170 | 179 | 177 | 176 | 165 | 170 | 174 | 171 | 171 |
| 12 | Hydrochlorothiazide | 20 | 4 | 164 | 161 | 159 | 161 | 159 | 163 | 152 | 151 | 149 |
| 13 | Hydrochlorothiazide | 40 | 5 | 168 | 167 | 167 | 164 | 163 | 161 | 159 | 155 | 155 |
| 14 | Hydrochlorothiazide | 80 | 5 | 169 | 152 | 160 | 142 | 145 | 145 | 141 | 141 | 140 |
| 15 | Carbidopa & Hydrochlorothiazide | 25 5 | 4 | 170 | 169 | 161 | 159 | 156 | 158 | 152 | 154 | 152 |
| 16 | Carbidopa & Hydrochlorothiazide | 25 20 | 4 | 170 | 164 | 164 | 163 | 155 | 162 | 158 | 158 | 153 |
| 17 | Carbidopa & Hydrochlorothiazide | 25 40 | 5 | 179 | 181 | 170 | 162 | 148 | 160 | 158 | 162 | 161 |
| 18 | Carbidopa & Hydrochlorothiazide | 25 80 | 6 | 176 | 153 | 146 | 146 | 128 | 135 | 133 | 138 | 146 |

[1]Dissolved in 1N HCl
[2]As Guanethidine sulfate dissolved in water
[3]Dissolved in 1N NaOH Table 2

Effect of hydralazine and clonidine, alone and in combination with carbidopa, on the mean arterial pressure of conscious SH rats.

| Group No. | Treatment | Dose mg/kg i.p. | No. of Rats | Mean Arterial Pressure, mm Hg, at hours after treatment |||||||||
|---|---|---|---|---|---|---|---|---|---|---|---|---|
| | | | | 0 | ½ | 1 | 2 | 4 | 8 | 12 | 18 | 24 |
| 1 | Saline | 2 ml/kg | 9 | 168 | 170 | 170 | 170 | 166 | 164 | 166 | 166 | 164 |
| 2 | Carbidopa[1] | 25 | 6 | 167 | 166 | 164 | 166 | 158 | 167 | 172 | 172 | 162 |
| 3 | Hydralazine[2] | 0.03 | 3 | 167 | 169 | 165 | 173 | 172 | 166 | 168 | 171 | 173 |
| 4 | Hydralazine | 0.125 | 4 | 170 | 166 | 165 | 166 | 171 | 174 | 168 | 168 | 167 |
| 5 | Hydralazine | 0.25 | 4 | 180 | 159 | 166 | 172 | 170 | 172 | 175 | 176 | 169 |
| 6 | Hydralazine | 0.5 | 9 | 164 | 128 | 138 | 146 | 152 | 161 | 160 | 160 | 159 |
| 7 | Hydralazine | 1 | 4 | 180 | 120 | 127 | 157 | 157 | 178 | 176 | 177 | 176 |
| 8 | Hydralazine | 2 | 5 | 169 | 120 | 126 | 135 | 144 | 152 | 156 | 154 | 162 |
| 9 | Carbidopa & Hydralazine | 0.312 0.125 | 4 | 166 | 158 | 146 | 154 | 153 | 166 | 164 | 163 | 157 |
| 10 | Carbidopa & Hydralazine | 1.25 0.125 | 4 | 163 | 155 | 142 | 145 | 151 | 156 | 147 | 147 | 151 |
| 11 | Carbidopa & Hydralazine | 5 0.125 | 4 | 168 | 187 | 175 | 166 | 163 | 135 | 133 | 130 | 152 |
| 12 | Carbidopa & Hydralazine | 25 0.03 | 4 | 174 | 163 | 157 | 144 | 138 | 152 | 160 | 163 | 160 |
| 13 | Carbidopa & Hydralazine | 25 0.125 | 5 | 177 | 137 | 132 | 149 | 140 | 149 | 151 | 155 | 158 |
| 14 | Carbidopa & Hydralazine | 25 0.25 | 4 | 173 | 146 | 147 | 158 | 158 | 159 | 164 | 164 | 170 |
| 15 | Carbidopa & Hydralazine | 1.25 0.5 | 6 | 169 | 143 | 149 | 156 | 159 | 161 | 157 | 165 | 166 |
| 16 | Carbidopa & Hydralazine | 5 0.5 | 6 | 172 | 134 | 129 | 143 | 150 | 152 | 152 | 149 | 154 |
| 17 | Carbidopa & Hydralazine | 25 0.5 | 8 | 175 | 117 | 115 | 130 | 141 | 149 | 153 | 153 | 153 |

Table 2-continued
Effect of hydralazine and clonidine, alone and in combination with carbidopa, on the mean arterial pressure of conscious SH rats.

| Group No. | Treatment | Dose mg/kg i.p. | No. of Rats | Mean Arterial Pressure, mm Hg, at hours after treatment | | | | | | | | |
|---|---|---|---|---|---|---|---|---|---|---|---|---|
| | | | | 0 | ½ | 1 | 2 | 4 | 8 | 12 | 18 | 24 |
| 18 | Clonidine[3] | 0.00075 | 4 | 170 | 171 | 171 | 170 | 169 | 166 | 172 | 161 | 170 |
| 19 | Clonidine | 0.003 | 4 | 169 | 166 | 156 | 165 | 163 | 165 | 168 | 177 | 179 |
| 20 | Clonidine | 0.0125 | 4 | 167 | 159 | 167 | 163 | 163 | 169 | 169 | 167 | 172 |
| 21 | Clonidine | 0.025 | 6 | 168 | 148 | 147 | 149 | 151 | 154 | 151 | 149 | 150 |
| 22 | Clonidine | 0.05 | 7 | 180 | 164 | 159 | 149 | 146 | 154 | 159 | 164 | 166 |
| 23 | Clonidine | 0.2 | 3 | 173 | 164 | 147 | 152 | 150 | 148 | 152 | 157 | 162 |
| 24 | Carbidopa & Clonidine | 25 0.00075 | 6 | 169 | 153 | 157 | 158 | 162 | 175 | 169 | 163 | 171 |
| 25 | Carbidopa & Clonidine | 25 0.003 | 6 | 168 | 134 | 141 | 146 | 150 | 148 | 151 | 152 | 162 |
| 26 | Carbidopa & Clonidine | 25 0.0125 | 5 | 166 | 144 | 139 | 143 | 154 | 161 | 167 | 170 | 164 |
| 27 | Carbidopa & Clonidine | 25 0.05 | 4 | 170 | 149 | 121 | 114 | 116 | 127 | 135 | 136 | 142 |
| 28 | Carbidopa & Clonidine | 1.25 0.05 | 4 | 180 | 156 | 149 | 148 | 151 | 159 | 171 | 170 | 175 |
| 29 | Carbidopa & Clonidine | 5 0.05 | 5 | 175 | 142 | 129 | 128 | 132 | 149 | 153 | 156 | 164 |

[1]Dissolved in 1N HCl
[2]As hydralazine . HCl Dissolved in water
[3]As clonidine . HCl Dissolved in 1N HCl The above data clearly shows the enhancement of anti-hypertensive properties of the non-reserpine, non-phenylalanine agent by the decarboxylase inhibitor.

Following are formulations of some representative dosage forms:

| Tablet Formulation | |
|---|---|
| Clonidine hydrochloride | 0.1 mg |
| Carbidopa | 5.0 mg |
| Calcium phosphate | 50.0 mg |
| Lactose | 20.0 mg |
| Starch | 10.0 mg |
| Magnesium sulfate | 0.5 mg |

| Liquid Suspension | |
|---|---|
| Guanethidine sulfate | 2.5 g |
| Carbidopa | 2.5 g |
| Veegum HV | 3.0 g |
| Methylparaben | 1.0 g |
| Kaolin | 10.0 g |
| Glycerin | 250.0 g |
| Water, q.s. ⟶ 1 liter | |

| Injectable Solution | |
|---|---|
| Hydralazine hydrochloride | 20 mg |
| Carbidopa .HCl | 100 mg |
| Distilled water, q.s. ⟶ 1 ml | |

| Capsule Formulation - I | |
|---|---|
| Hydrochlorothiazide | 50 mg |
| Carbidopa | 15 mg |
| Lactose | 50 mg |
| Talc | 3 mg |

| Capsule Formulation - II | |
|---|---|
| Clonidine HCl | 0.2 mg |
| Carbidopa | 100.0 mg |
| Mannitol | 98.0 mg |
| Stearic acid | 1.0 mg |

While the test results were obtained by i.p. administration of the two drugs of the present composition separately, the effect is demonstrative of the anti-hypertensive effect which would be obtained on administration, orally or parenterally, of the hypotensive agent and decarboxylase inhibitor either as a combination or individually and simultaneously. Another embodiment of this invention is a method of treating hypertensive animals by thus administering an anti-hypertensive amount of the aforesaid composition comprising the hypotensive agent and the decarboxylase inhibitor.

The term animals includes humans.

Claims to the invention follow.

What is claimed is:

1. A pharmaceutical composition for treating hypertension comprising effective amounts of
   a. hydralazine or a pharmaceutically acceptable salt thereof and
   b. racemic mixture or L-isomer of a hydrazino phenyl propionic acid decarboxylase inhibitor,
   wherein the weight ratio of (a):(b) is 1:1 to about 1:1000.

2. The pharmaceutical composition of claim 1 wherein said decarboxylase inhibitor has the formula:

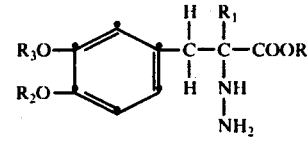

wherein R, $R_1$, $R_2$ and $R_3$ are independently selected from hydrogen and $C_1$-$C_4$-alkyl, and pharmaceutically acceptable salts thereof.

3. The composition of claim 2 wherein R, $R_2$, and $R_3$ are hydrogen and $R_1$ is methyl and said (b) inhibitor is the L-isomer, substantially free of the D-isomer.

4. The composition of claim 3 wherein said (a) is hydralazine hydrochloride.

5. A method for treating hypertensive animals which comprises administration of 0.2 mg/kg to 1000 mg/kg per day of the claim 1 composition.

* * * * *